United States Patent [19]

Elias

[11] Patent Number: 4,698,071
[45] Date of Patent: Oct. 6, 1987

[54] TRACE VAPOR CONCENTRATOR

[75] Inventor: Lorne Elias, Nepean, Canada

[73] Assignee: Canadian Patents and Development Limited, Ottawa, Canada

[21] Appl. No.: 850,524

[22] Filed: Apr. 11, 1986

[30] Foreign Application Priority Data

Apr. 15, 1985 [CA] Canada .................................. 479118

[51] Int. Cl.⁴ ............................................. B01D 53/08
[52] U.S. Cl. .......................................... 55/28; 55/60;
55/79; 55/181; 55/208; 55/390
[58] Field of Search .................... 55/17, 34, 58, 60, 74,
55/75, 77, 79, 80, 82, 180, 181, 208, 387, 390, 28

[56] References Cited

U.S. PATENT DOCUMENTS

| | | | |
|---|---|---|---|
| 2,391,334 | 12/1945 | Nicholson | 55/79 X |
| 2,397,566 | 4/1946 | Schutte | 55/181 |
| 2,493,911 | 1/1950 | Brandt | 55/79 |
| 2,515,134 | 7/1950 | Murphree | 55/79 X |
| 2,580,635 | 1/1952 | Winter, Jr. | 55/82 X |
| 2,603,608 | 7/1952 | Lewis et al. | |
| 2,607,440 | 8/1952 | Lewis | 55/82 X |
| 3,016,107 | 1/1962 | Strange et al. | |
| 3,190,867 | 6/1965 | Oldweiler et al. | |
| 3,405,508 | 10/1968 | Peters et al. | 55/77 X |
| 3,438,178 | 4/1969 | Betteridge et al. | 55/58 |
| 3,568,411 | 3/1971 | Dravnieks et al. | 55/208 |
| 3,798,877 | 3/1974 | Lamb | 55/79 |
| 3,967,928 | 7/1976 | Schmidt et al. | 73/23 X |
| 3,998,734 | 12/1976 | Barringer | 55/17 X |

FOREIGN PATENT DOCUMENTS 1339621 12/1973 United Kingdom .

OTHER PUBLICATIONS

"New Concepts Symposium and Workshop", Oct. 30 to Nov. 1/78, Reston, Va., U.S.A.
M. Krzymien and L. Elias, "A Continuous-Flow Trace Vapour Source", National Aeronautical Establishment, National Research Council of Ottawa, Canada, Journal of Physics E: Scientific Intruments, 1976, vol. 9, pp. 584-586.
L. Elias and M. Krzymien, Laboratory Technical Report, "Method of Evaluating Sensitivity of Explosives Vapour Detectors", Jan. 1975, National Research Council, Ottawa, Canada.

Primary Examiner—Robert Spitzer
Attorney, Agent, or Firm—Robbins & Laramie

[57] ABSTRACT

The specification discloses a method and apparatus for concentration of vapors present in trace quantities in the atmosphere in a continuous and rapid manner. It relates especially to a device to enhance the concentration of trace vapors to such a level that they may be more readily analyzed by appropriate instrumentation. This is of considerable value in connection with the detection of certain vapors which are associated with explosive devices and bombs. These are of considerable importance now in connection with security at airports and the like. The specification discloses a method and apparatus for the continuous concentration of trace gases in a gaseous medium, such as air, comprising the steps of bringing the air into intimate contact with a suitable free-flowing adsorption powder in an adsorption region, passing the air containing the treated powder and adsorbed vapors through a cyclone separator to produce a substantially powder-free air stream and a powder containing adsorbed vapors, then passing the powder through a desorption region whereby the powder carrying trace vapors is heated in a heating zone in the presence of a carrier stream at a temperature sufficient to release the adsorbed trace vapors of interest, and thus to produce a vapor-enriched carrier gas stream. The powder is then normally recycled into the air inlet stream.

31 Claims, 5 Drawing Figures

CHROMATOGRAMS OF EGDN ANALYSIS. EGDN RETENTION TIME 1.74 MIN. a) 3.2 pg, SAMPLE VOLUME 400 cm³
b) 87 pg, SAMPLE VOLUME 10 cm³   c) 86 pg, 8 μL STANDARD SOLUTION

FIG. 4

TRACE VAPOR CONCENTRATOR

The specification discloses a method and apparatus for concentration of vapours present in trace quantities in the atmosphere in a continuous and rapid manner. It relates especially to a device to enhance the concentration of trace vapours to such a level that they may be more readily analyzed by appropriate instrumentation. This is of considerable value in connection with the detection of certain vapours which are associated with explosive devices and bombs. These are of considerable importance now in connection with security at airports and the like. The specification discloses a method and apparatus for the continuous concentration of trace gases in a gaseous medium, such as air, comprising the steps of bringing the air into intimate contact with a suitable free-flowing adsorption powder in an adsorption region, passing the air containing the treated powder and adsorbed vapours through a cyclone separator to produce a substantially powder-free air stream and a powder containing adsorbed vapours, then passing the powder through a desorption region whereby the powder carrying trace vapours is heated in a heating zone in the presence of a carrier stream at a temperature sufficient to release the adsorbed trace vapours of interest, and thus to produce a vapour-enriched carrier gas stream. The powder is then normally recycled into the air inlet stream.

BACKGROUND DISCUSSION

The present invention relates to a method and apparatus for the concentration of gases and vapours present in trace quantities in the atmosphere or in some other gaseous medium. In this specification the gases and vapours which are of interest will be referred to as "vapours". Such vapours normally are gaseous forms of materials which may be gaseous, liquid or solid at room temperature, or those which are emitted from liquids and solids at room temperature. They will also embrace in this connection certain gases which are not considered vapours but which are capable of being adsorbed onto adsorption powders for removal from an air stream or the like.

Specifically the invention relates to a device and method for enhancing the concentration of trace gases and vapours to such a level that they may be more readily analyzed by appropriate instrumentation.

A great deal of work has been done in recent years to facilitate the work of detecting bombs in various situations, such as in maintaining security at airports and in boarding aircraft. X-ray machines and manual searches are, of course, invaluable but cannot be expected to detect all types of weapons such as explosives.

The devices already known involve the preconcentration of vapours in discrete volumes of air. A measured volume of sample air is passed through a solid or liquid filter which collects the vapours of interest. The collected vapours are subsequently retrieved in a much more concentrated form than originally prevailing in the atmosphere. If the volume of air sampled is large enough, sufficient vapour may be recovered to be amenable to analysis. This basically constitutes a batching-sample method and is therefore time consuming and generally unsuitable for real time requirements.

In U.S. Pat. No. 2,493,911, issued on Jan. 10, 1950, to P. L. Brandt, an adsorption powder is continuously recirculated through cool adsorption and hot desorption regions to effect separation of the desired components. The process described by Brandt requires relatively large quantities of adsorbent powder for its industrial applications, and it is relatively expensive to use. The large amount of powder involved also places a constraint on the speed of operation of the adsorption-desorption process. The Brandt patent relies on the evolution of relatively large quantities of gas during the desorption phase to transport the adsorption powder from a low to a high elevation, which would not be effective when attempting to separate and concentrate minute traces of gases from the mixture as in the present invention.

Also known in the prior art is the use of a cyclone separator to remove naturally prevailing dust particles in the atmosphere for the purpose of subjecting them to elemental analysis. This is used in geographical surveys and has been developed, for example, by Barringer Research Limited of Toronto, Canada, (see U.S. Pat. No. 3,998,734 issued Dec. 21, 1976, of A. R. Barringer).

The present inventor has been involved in an ongoing research programme to develop the present invention, as summarized in the proceedings of "New Concepts Symposium and Workshop", Oct. 30 to Nov. 1, 1978, Reston, Virginia, U.S.A., published by The U.S. Departments of Treasury, Energy, Justice and Transportation, pages 265 to 267, the contents of which are incorporated herein by reference.

OBJECTS OF THE INVENTION

The object of the present invention is to provide a more efficient method and means for preconcentrating gases and vapours in air or other gaseous media than has heretofore been known, a method that will require a minimum of expense, and means which allows preconcentration of gases or vapours on a continuous basis with little or no time lag.

A further object of the invention is to effect the transfer of the powder from a test medium to the carrier gas.

Another object of one aspect of the invention is the continuous recycling of the sample powder from the desorption region to the adsorption region of the device.

A specific object of the invention is to provide a device which is readily portable and is suitable for use in concentrating extremely small quantities of gases and vapours. Other objects will become apparent as the detailed description of the invention proceeds.

The device of the present invention collects the vapours of interest from the sampled air by means of adsorbent powder. The collection of the vapours on the powder and their subsequent removal through desorptive heating and transfer to an auxiliary carrier gas stream comprises an efficient concentrating effect. One important feature of this device is that instead of scrubbing pertinent vapours from discrete volumes of air by a stationary bed of adsorbent material as shown in the prior art, resulting in a discontinuous and time-consuming concentration process, it now becomes possible to achieve a similar concentrating effect on a continuous and nearly instantaneous basis. It is, moreover, possible to attain a high degree of specificity with regard to the vapour being collected, through selection of the adsorbent powder, the adsorption temperature, and the desorption temperature.

SUMMARY OF THE INVENTION

Figure 1:
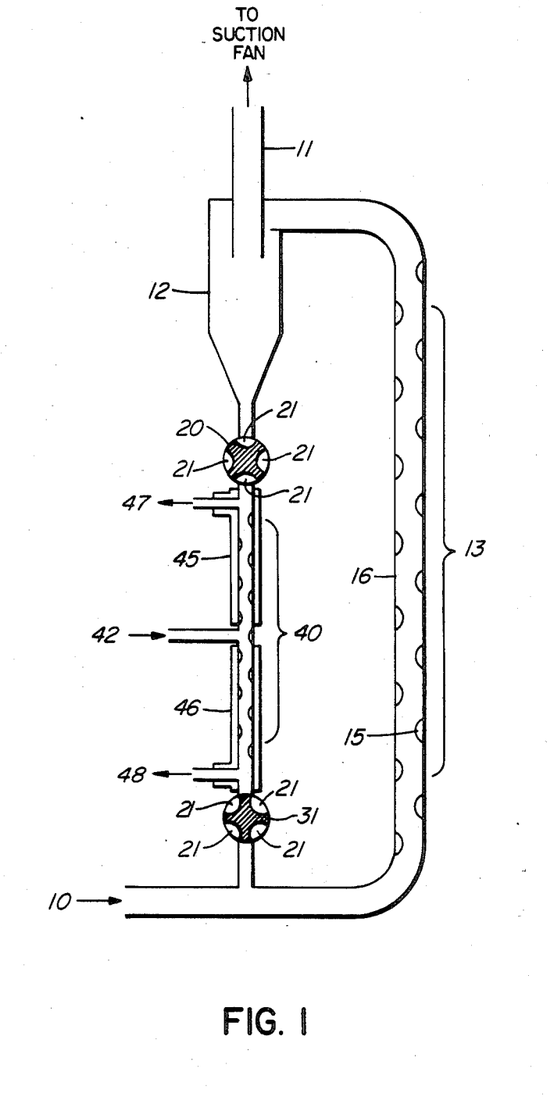

The present invention allows for the preconcentration of gases and vapours present in trace quantities in various gaseous media including the atmosphere and a portable device to enhance the concentration of these trace gases on a continuous basis with little or no time lag, such that the resultant sample is concentrated to such a level that it may be more readily analyzed by appropriate instrumentation.

An important use of the present invention is for the detection of hidden explosives, based on analysis of ambient air for traces of characteristic vapours. The inventor has found that this device and method is capable of converting certain trace vapours present in parts-per-trillion (ppt) (1 pt$=10^{-12}$ mole fraction) into a much more readily measurable concentration of parts-per-billion (ppb) (1 ppb$=10^{-9}$ mole fraction) in a carrier gas.

Thus the present invention provides a method for the rapid and continuous concentration of trace vapours in a gaseous medium comprising the steps of entraining an adsorption powder for the trace vapours in a stream of the gaseous medium in an adsorption region, passing the gaseous stream containing the powder and adsorbed vapour through a particle separator to produce a substantially powder-free sample gas and to collect the powder containing adsorbed vapours, then passing the powder through a desorption region in contact with a carrier gas stream, the powder being heated sufficiently in the desorption region to release the adsorbed trace vapours into the carrier stream, and then recovering the carrier gas with the desorbed vapours from the powder.

In a preferred embodiment of such a method the adsorption powder containing the adsorbed vapours is passed into a first desorption region heated to a suitable temperature for removal of the vapours desired to be tested, and then the powders are passed through a heated zone at a higher temperature to complete the removal of other vapours therefrom, the carrier gas from the second heating zone being vented.

In connection with certain preferred embodiments the temperature of adsorption is approximately room temperature and the temperature of desorption is 120° to 150° C. The carrier stream will normally be nitrogen gas. The adsorbent powder will normally be in the range of 60 to 120 mesh size.

The heating zones are suitably adapted to heat the powder, for example by contact with the walls of the desorption region, or by inductive means (for example radio frequency or microwave), or radiant heating means. The walls may suitably be heated by an electrical resistance heating coil.

In a preferred embodiment of such a method, the desorption region has two heated zones, the first heated zone having a first temperature $T_1$ suitable for desorption of the vapour of principal interest and the second heated zone has a second temperature $T_2$ which is higher than $T_1$, and is suitable for removing substantially all vapours from the adsorption powder.

The present invention also provides a continuous trace vapour preconcentrator comprised of a gaseous medium sample inlet, a vapour adsorption region, a particle separator, a vapour desorption region, and a vapour takeoff outlet; wherein said inlet allows for the introduction of a stream of sample gaseous medium and a quantity of suitable adsorbent powder; said adsorption region provides mixing of the sample flow resulting in contact of the powder with the sample stream; said separator is adapted to separate the powder with adsorbed vapours from the gaseous sample stream; said desorption region has a heating zone and means for the introduction of a low flow carrier stream; and said vapour takeoff outlet allows for the removal of the carrier stream with enriched vapour concentrate, said carrier stream having a low flow rate relative to the flow rate of the gaseous sample stream.

The preconcentrator is normally further provided with a means for collection of the desorbed powder and means for recycling the powder to the inlet for reuse.

BRIEF DESCRIPTION OF THE DRAWINGS

In the accompanying drawings which illustrate, by way of example, embodiments of the present invention:

FIGS. 1, 1(*a*) and 2 depict schematic representations of embodiments of a continuous trace vapour preconcentrator, also referred to herein as a continuous-action preconcentrator, or CAP.

FIG. 3 shows chromatograms resulting from analysis of ethylene glycol dinitrate (EGDN), which is a typical vapour associated with explosives of the type of concern in airports.

FIG. 4 illustrates response time when a flame ionization detector (FID) is coupled to the continuous action preconcentrator of FIG. 1.

DETAILED DISCLOSURE

In the embodiment shown in FIG. 1, sample air is drawn through the inlet (10) from the area to be tested. This can be achieved by a suction pump connected to the outlet (11) of the cyclone particle separator (12) or by a positive action blower fan in the circuit at the sample air inlet. A quantity of a suitable adsorbent powder is introduced into the sample stream at the sample air inlet and is swept along by the flow. The powder will normally be in the 60 to 120 mesh size range. Suitable powders include usual chromatographic packings and solid absorbants. Examples of such powders are TENAX-GC (trade mark), CHROMOSORB (trade mark) coated with a silicone type stationary phase such as OV-1 or OV-17 (trade marks); charcoal, silica gel, molecular sieve, nickel powder; or any of the other packings conventionally used in gas chromatography. The choice of the particular adsorbent powder will depend on the parameters of the system, including the type of gas or vapour to be adsorbed and the conditions of temperature and the like to be used in the system.

In the embodiment shown in FIG. 1 some increase in turbulence is induced and promoted in the adsorption region (13) by indentations (15) in the walls of the flow tube (16) for intimate contact of the powder with the sample stream. The adsorption region will normally be operated at room temperature. For certain specific applications it may be warmed or alternatively cooled for selectivity in adsorption of vapours. The choice of such conditions will be obvious to a person skilled in the art or will be determined by ordinary experimentation.

The adsorption powder loaded with the trace vapours from the sample air is then passed to a cyclone particle separator (12) where the powder is removed from the air stream and falls to the bottom of the cyclone separator. The cyclone separator is a simple device of known construction and operation. The air stream is passed out of the system through outlet (11), and will not normally be of any further interest.

In the embodiment shown in FIG. 1, the adsorbent powder which has been removed from the air stream and has collected at the bottom of the cyclone particle separator (12) is then passed into a desorption region. In the embodiment shown in FIG. 1 there is a valve driven by a motor (20), suitably at about one revolution per second. With the four valve pockets (21) shown in FIG. 1 this provides a flow of powder from the sample air to the desorption region (40) without any significant flow of sample air into the desorption region. In fact some slight flow of nitrogen carrier gas from the desorption region (40) to the particle separator (12) may occur as a result of the positive pressure of nitrogen carrier gas.

The desorption region (40) consists of two heated zones (45) and (46), in the embodiment shown in FIG. 1. Heated zone (45) is heated to temperature $T_1$, which is sufficient to cause the desorption of the particular trace vapours desired, which are taken up by the carrier gas, such as nitrogen, introduced in carrier inlet (42), and are taken off through vapour takeoff (47). The vapour takeoff will of course go to an analyzer. This may be any real time analyzer, such as a mass spectrometer, ion mobility spectrometer, or ionization detector.

Heated zone (46) in this particular embodiment is at a somewhat higher temperature $T_2$ for "cleanup" of the vapours and materials which may be adsorbed in the powder. Vent (48) can be adjusted for bleeding off a sufficient amount of the nitrogen carrier from heated zone $T_2$ to provide a suitable amount of vapour takeoff at outlet (47), containing the vapours of principal interest. The powder which has by then fallen to the bottom of the desorption region (40) is then fed back into the sample air inlet for recycling. A motor driven valve (31), similar to valve (20), may suitably be used for this purpose, to provide positive displacement of the powder without any appreciable air flow. This cycle of powder entering the air inlet flow, passing through the adsorption region, the cyclone particle separator, and the desorption region, can occupy as little as a few seconds. Thus this provides a continuously available reading of the vapour concentrations in the incoming air.

An estimate of the vapour enrichment achievable with the device is readily calculated. If the sample air containing a concentration $C_i$(air) of a particular trace component i is sampled at a rate of F(air), the maximum enrichment ratio $$\frac{C_i(N)}{C_i(\text{air})} = \frac{F(\text{air})}{F(N)}$$

where $C_i$(N) refers to the vapour concentration at the takeoff point and F(N) is the flow rate of the nitrogen stream at the same exit. If both the adsorption and desorption processes are complete, that is to say all of the i-component is removed from the sampled air flow and retrieved in the $T_1$ zone, then for typical operating flow rates of F(air)=100 L/min (liters per minute) and F(N)=0.1 L/min $$\frac{C_i(N)}{C_i(\text{air})} = 10^3$$

Thus, in this example, there has been a thousandfold increase in the concentration of the desired trace component.

The choice of the arrangement and temperatures involved in heated zone $T_1$ and $T_2$ can be varied. Normally, heated zone 46 is at a sufficiently high temperature $T_2$ to remove all vapours and gases so that the powder leaving the desorption region is substantially free of adsorbed material. However, the temperature $T_2$ of heated zone (46) may be chosen for removal of a second desired vapour (or gas as mentioned earlier) and, in fact, one or more additional heated zones may be provided with various temperatures and levels of removal of vapours from the powder.

In some cases the use of different temperatures $T_1$ and $T_2$ may be advantageous, for desorption of thermally labile vapours such as EGDN at a lower temperature, and for desorption of higher boiling-point vapours such as DNT at a higher temperature, in the embodiments shown in the Figures.

The embodiment shown in FIG. 1 employs gravity to pass the powder through the desorption region and collect it at the end of that region. By suitable variations of the structure and method, an embodiment can be provided which is not gravity dependent.

The carrier gas introduced at carrier inlet (42) will normally be an inert gas, such as nitrogen. This can have certain advantages over the use of air as the carrier gas, since some adsorption powders and some vapours will be degraded by oxidation after repeated passes through a heated zone in the presence of air.

Although almost all of the adsorption powder is recovered in the cyclone particle separator (12) there will be a certain amount of powder lost through the sample outlet (11). It is possible to extend the operational life of the system before requiring an introduction of additional powder by providing a powder reservoir at the bottom of the desorption zone (40) immediately above valve (31).

In another embodiment shown in FIG. 1(*a*) the nitrogen carrier is introduced through input parts (32) and (33). The vapour take-off port is shown as (36). The heated zones (45) and (46) will normally be at the same temperature, suitable for desorbing the vapours of interest, in this embodiment. The chromatograms and tracings of FIGS. 3 and 4 resulted from operation of the CAP shown in FIG. 1(*a*).

Although a motor driven valve with four pockets is shown in FIGS. 1 and 1(*a*), other means may be used for introducing the powder into the desorption region without permitting significant flow of sample air therein, and likewise for re-introducing the powder into the sample air stream.

For example, in the embodiment shown in FIG. 2, a constriction (53) is shown in place of the previous rotating valve (20) at the inlet of the desorption zone, while a powder reservoir (52) and metering valve (51) are shown in place of the previous rotating valve (31) at the bottom of the desorption zone. When a blower fan (50) or some other positive pressure device is employed at the inlet (10) to provide a sample air stream, positive pressure is maintained in the cyclone particle separator (12), and by suitable choice of carrier gas pressure introduced at carrier inlet (42), the bulk of the sample air will be forced out of the sample air outlet (11) and only a very minor portion of it will descend into the desorption region (40) with the powder.

Similarly, in the embodiment shown in FIG. 2, the powder reservoir (52) acts as a boundary to keep separate the incoming sample air stream from the carrier stream at the bottom of the desorption zone (40). The powder metering valve (51) functions as a means of introducing adsorbent powder into the system at a desired rate.

The apparatus of the present invention may be adapted for transportation and on-site use. The desorption region may have an effective diamer of 2 to 8 mm, and a length of 30 to 100 cm. The adsorption region may have an effective diameter of 1 to 3 cm, and a length of 70 to 200 cm.

EXPERIMENTAL VERIFICATION

Figure 1A:
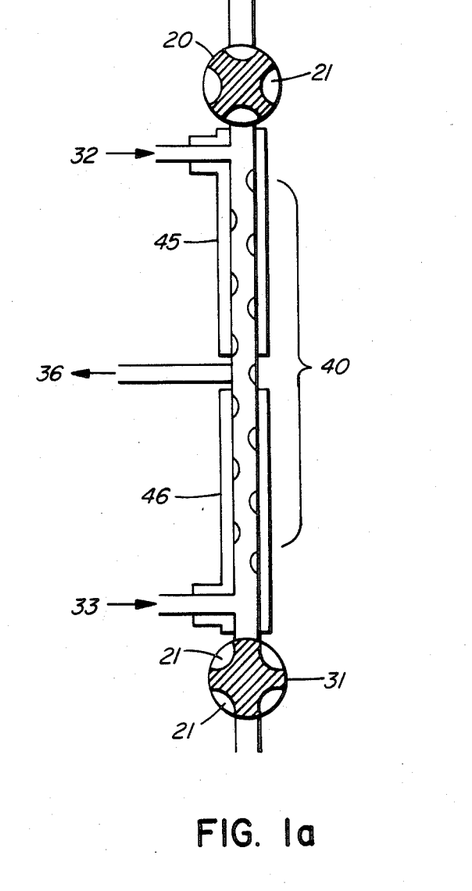
Figure 2:
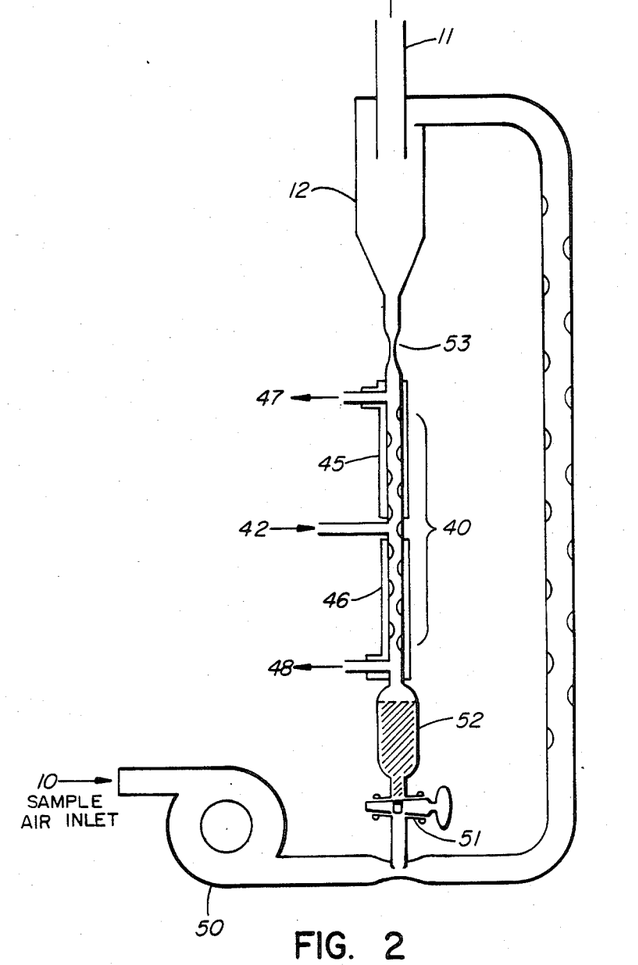

The concept of vapour enhancement embodied in this continuous action preconcentrator invention has been validated experimentally using a rudimentary, nonoptimized configuration of the device shown schematically in FIG. 1(a), constructed in large part with readily available standard components. Some of the test procedures employed and data obtained are outlined below.

A. Determination of Enrichment Ratio. A trace vapour generator, similar to that described by Krzymien and Elias in J. Phys. E: Sci. Inst., 9, 584 (1976), (the contents of which are incorporated herein by reference) was used to provide known, controllable concentrations of ethylene glycol dinitrate (EGDN) vapour in an air stream. The latter, flowing at a rate in excess of 500 L/min, contained part-per-trillion (ppt) levels of EGDN (1 ppt = $10^{-12}$ mole fraction), which was determined by gas chromatography, using the sampling and analysis protocol described in NRC Laboratory Technical Report LTR-UA-27, (National Research Council - Canada) Jan. 1975 - L. Elias and M. Krzymien, (the contents of which are incorporated herein by reference).

The continuous action preconcentrator was operated with its inlet (10) in the spiked air stream, while samples were taken and analyzed of the nitrogen carrier stream at the outlet end (36) (the Vapour Takeoff port) of the device. The ratio of EGDN concentration at the outlet C(N) to that at the inlet C(air) comprised the observed enrichment ratio.

Two series of tests are summarized in Table I, in which enrichment factors of 2-3 orders of magnitude were achieved. Although well below the theoretical maximum (based on F(air)/F(N)), the results clearly illustrate the capability of the invention to concentrate trace vapour levels in ambient air to very much higher values.

Figure 3:
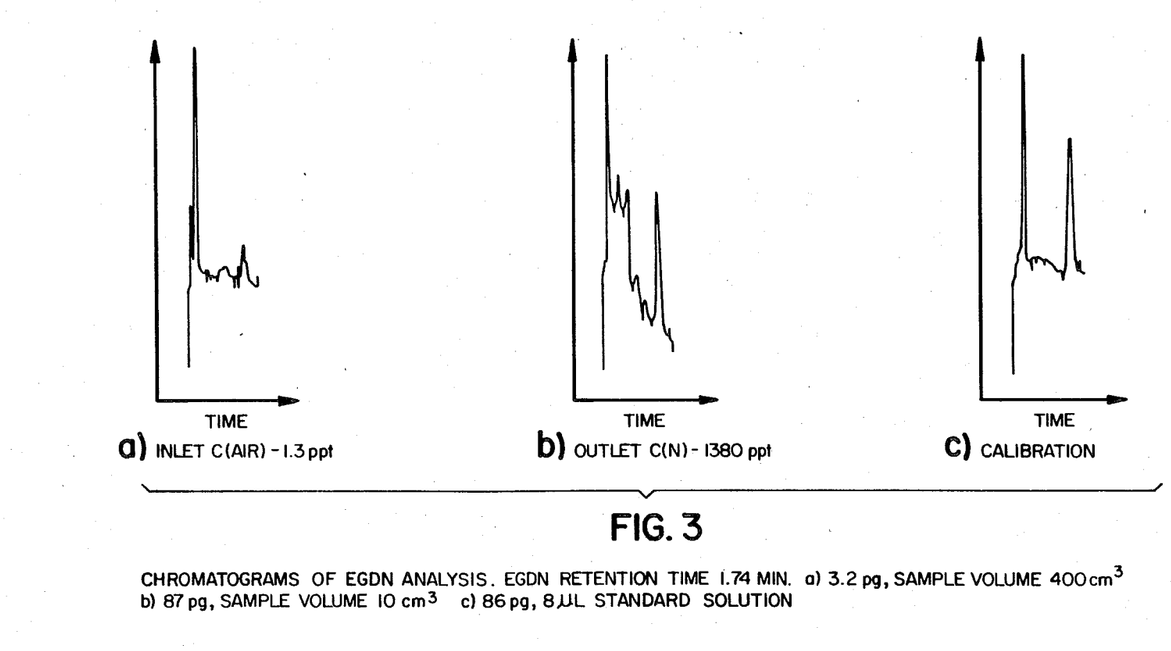

FIG. 3 presents typical chromatograms obtained from analysis of the inlet and outlet streams.

FIGS. 3a and 3b show respectively the EGDN concentrations in the inlet air and the outlet carrier gas (nitrogen) and it can be seen that there is a thousand fold increase in concentration. In FIG. 3(a) 3.2 picograms (pg) in a sample volume of 400 cm$^3$ were analyzed. In FIG. 3(b) chromatographic analysis yielded 87 pg of EGDN in a sample volume of 10 cm$^3$.

FIG. 3c shows a calibration run involving 86 picograms ($10^{-12}$ grams) in 8 microliters standard solution. The area under the peak at 1.74 shows quantitatively the concentration of the vapour.

B. Speed of Response. To test the response time of the continuous action preconcentrator (CAP) to a sudden change of the incoming vapour concentration, a flame ionization detector (FID) was connected to the outlet port to continuously monitor C(N). Target vapours utilized in these trials were acetone and propane. CAP operating conditions were: adsorbent powder - Tenax GC; $T_1/T_2$ -200°/200° C.; F(N) - 50 mL/min; F(air) - 53 L/min.

Figure 4:
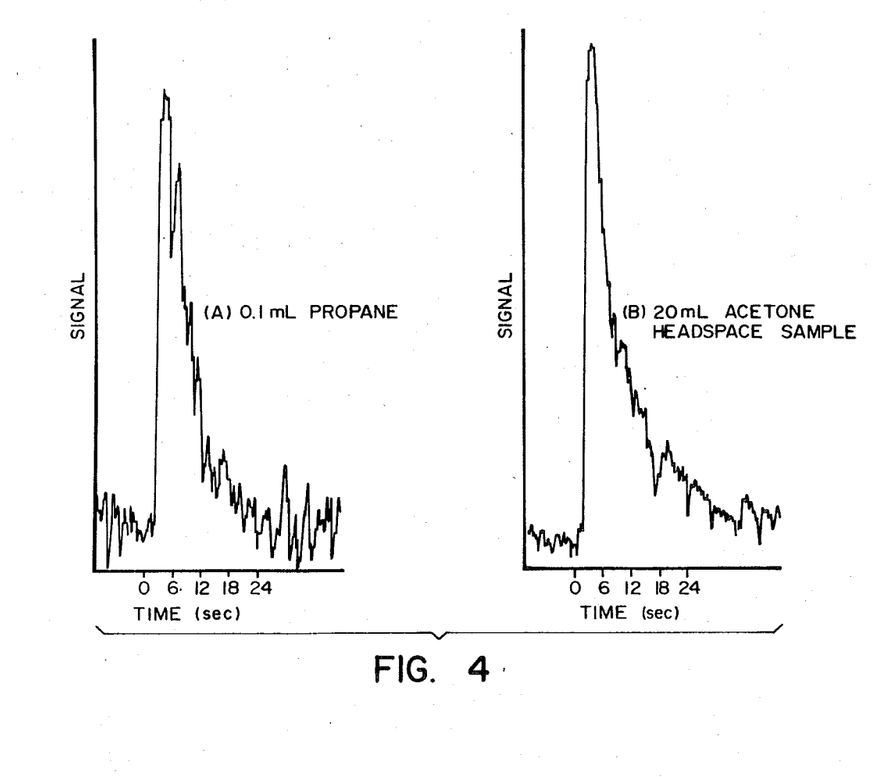

In one experiment, 0.1 mL of propane (FIG. 4(a)) was fed into the inlet while the FID signal was recorded. In another experiment a 20 mL headspace sample from acetone (FIG. 3a), obtained with a gas-sampling syringe, was rapidly injected into the inlet of the CAP while operating in normal room air. Tracings from these trials are shown in FIG. 4.

An overall time lag of 3-5 seconds is evident from FIG. 4, most of which may be due to the time required to transport the vapours through the connecting line of the FID.

As can be seen from FIGS. 4a and 4b, introduction of propane and acetone into the system resulted in a very prominent response at about 3 seconds, peaking at about 6 or 7 seconds, and tapering off over the next 18 to 20 seconds.

TABLE I

| | Determination of Enrichment Ratio C(N)/C(air) for EGDN Vapour | | | | | | |
|---|---|---|---|---|---|---|---|
| | | | | | EGDN Conc. | | |
| Run No. | Adsorbent | $T_1/T_2$ | F(N) mL/min | F(air) L/min | C(air) ppt | C(N) ppt | $\dfrac{C(N)}{C(air)}$ |
| R117 | Tenax*-GC | 120°/120° C. | 20 | 72 | 4.1 | 970 | 240 |
| 118 | Tenax*-GC | 120°/120° | 20 | 72 | 4.1 | 1200 | 300 |
| 119 | Tenax*-GC | 120°/120° | 20 | 72 | 4.1 | 1100 | 270 |
| 301 | Chromosorb* | 150°/150° C. | 12 | 53 | 1.3 | 1700 | 1300 |
| 310 | Chromosorb* | 150°/150° | 12 | 53 | 1.3 | 1400 | 1100 |
| 312 | Chromosorb* | 150°/150° | 12 | 53 | 1.3 | 1900 | 1500 |
| 320 | Chromosorb* | 150°/150° | 12 | 53 | 1.3 | 2100 | 1600 |

*trade marks.

As will be understood by any person skilled in the art, the present invention is amenable to variations on the structural details and parameters of operation of the present invention.

I claim:

1. A method for the rapid and continuous concentration of trace vapours in a gaseous medium comprising the steps of entraining an adsorption powder for the trace vapours in a stream of the gaseous medium in an adsorption region, passing the gaseous stream containing the powder and adsorbed vapour through a particle separator to produce a substantially powder-free sample gas and to collect the powder containing adsorbed vapours, passing the powder through a desorption region in contact with a carrier gas stream, heating the powder sufficiently in the desorption region to release the adsorbed trace vapours into the carrier stream, and then recovering the carrier gas with the desorbed vapours from the powder.

2. A method as in claim 1 wherein the adsorption powder containing the adsorbed vapours is passed into a first desorption region heated to a suitable temperature for removal of the vapours desired to be concentrated, and then the powder is passed through a second heated zone at at a higher temperature to complete the removal of vapours therefrom, the carrier gas from the second heated zone being vented.

3. A method as in claim 1 wherein the vapour is ethylene glycol dinitrate (EGDN).

4. A method as in claim 3 wherein the temperature of adsorption is approximately room temperature and the temperature of desorption is 120° to 150° C.

5. A method as in claim 1 wherein the carrier stream is nitrogen gas.

6. A method as in claim 1 wherein the adsorption powder is of a size in the range of 60 to 120 mesh size.

7. A method as in claim 1 further comprising a means for collection of the powder after desorption and means for recycling the powder to the stream of gaseous medium for reuse.

8. A method as in claim 1 wherein said desporption region has two heated zones, the first heated zone having a first temperature $T_1$ suitable for first desorption of vapours, and the second heated zone having a second temperature $T_2$ which is higher than $T_1$, and which is suitable for removing vapours of principal interest from the adsorption powder for recovery.

9. A method as in claim 1 wherein the adsorption powder containing the adsorbed vapours is passed into a first desorption region heated to a suitable temperature for removal of the vapours desired to be concentrated, and then the powders are passed through a heated zone at a higher temperature to complete the removal of vapours therefrom, and wherein the desorption region comprises two carrier gas inlets disposed at the beginning and end of the desorption region, and a carrier gas and vapour recovery outlet intermediate said inlets.

10. A method as in claim 1 wherein the powder is passed through the bottom of the particle separator by gravity feed through a powder feed zone, said powder feed zone being provided with a constriction for the purpose of preventing excess downward flow of the sample gaseous medium into the carrier gas in the desorption region, said sample gaseous medium being introduced into the adsorption region under positive gaseous pressure.

11. A method as in claim 10 wherein the positive gaseous pressure is provided by a blower fan.

12. A method as in claim 1 wherein a reservoir of adsorbent powder is maintained adjacent to the exit from the desorption region, and is metered therefrom into the stream of gaseous medium.

13. A method as in claim 1 wherein the powder is passed through the bottom of the particle separator by gravity to a powder feed zone, said powder feed zone comprising a rotary positive displacement metering valve means.

14. A method as in claim 1 wherein the powder in the desorption region is heated by contact with the walls of the desorption region or by induction or radiation heating means.

15. A method as in claim 1 wherein the ratio of gaseous medium flow to carrier gas flow is in the range of 10:1 to $10^6$:1.

16. A method as in claim 15 wherein the ratio is in the range of 100:1 to 10,000:1.

17. A method as in claim 15 wherein the ratio is in the order of 1,000:1.

18. A method as in claim 1 wherein the vapour is 2,4-dinitrotoluene (DNT) and the desorption is carried out at a temperature in the range of 130° to 180° C.

19. A continuous trace vapour preconcentrator comprised of a gaseous medium sample inlet, a vapour adsorption region, a particle separator, a vapour desorption region, and vapour takeoff outlet; wherein said inlet allows for the introduction of a stream of sample gaseous medium and a quantity of suitable adsorbent powder; said adsorption region provides mixing of the sample flow resulting in contact of the powder with the sample stream; said particle separator is adapted to separate the powder with adsorbed vapours from the gaseous sample stream; said desorption region has a heating zone, means for heating the heating zone, and means for the introuduction of a low flow carrier stream; and said vapour takeoff outlet allows for the removal of the carrier stream with enriched vapour concentrate, said carrier stream having a low flow rate relative to the flow rate of the gaseous sample stream.

20. An apparatus as in claim 19 which is adapted for transportion and on-site use, wherein the desorption region has an effective diameter of 2 to 8 mm, and a length of 30 to 100 cm.

21. An apparatus as in claim 20, wherein the adsorption region has an effective diameter of 1 to 3 cm, and a length of 70 to 200 cm.

22. An apparatus as in claim 19 wherein the desorption region comprises a first desorption zone heated to a suitable temperature for removal of the vapours desired to be concentrated, a second desorption zone at a higher temperature to complete the removal of vapours therefrom, means for heating the first and second desorption zones to different temperatures, and means for venting the carrier gas from the second desorption zone.

23. An apparatus as in claim 22 wherein the desorption region comprises two carrier gas inlets disposed at the beginning and end of the desorption region, and a carrier gas and vapour recovery outlet intermediate said inlets.

24. An apparatus as in claim 19 further comprising a means for collection of the powder after desorption and means for recycling the powder to the inlet for reuse.

25. An apparatus as in claim 19 wherein said desorption region has two heated zones, the first heated zone having a first temperature $T_1$ suitable for first description of vapours, and the second heated zone having a second temperature $T_2$ which is higher than $T_1$, and which is suitable for removing vapours of principal interest from the adsorption powder for recovery.

26. An apparatus as in claim 19 wherein the bottom of the particle separator is provided with a powder feed zone, aid powder feed zone including a constriction adapted to prevent excess downward flow of the sample gaseous medium into the carrier gas in the desorption region, and means for maintaining the sample gaseous medium in the adsorption region under positive gaseous pressure.

27. An apparatus as in claim 19 including a reservoir for adsorbent powder adjacent to the exit from the desorption region, and means for metering the powder therefrom into the gaseous medium sample inlet.

28. An apparatus as in claim 19 wherein the particle separator is a cyclone separator, and the cyclone separator is provided with a powder feed zone, said powder feed zone comprising a rotary positive displacement metering valve.

29. An apparatus as in claim 19 wherein the desorption region is provided with means for heating the powder by contact with the walls of the desorption region.

30. An apparatus as in claim 19 wherein the desorption region is provided with means for heating the powder by induction.

31. An apparatus as in claim 19 wherein the desorption region is provided with means for heating the powder by radiation.

* * * * *